United States Patent [19]

Pinsky

[11] 4,134,798

[45] Jan. 16, 1979

[54] ISOCYANURATE SPECIFIC ELECTRODE AND METHOD OF ANALYSIS AND QUATERNARY AMMONIUM ISOCYANURIC ACID SALTS THEREFORE

[75] Inventor: Michael L. Pinsky, Mount Holly, N.J.

[73] Assignee: FMC Corporation, Philadelphia, Pa.

[21] Appl. No.: 885,499

[22] Filed: Mar. 13, 1978

[51] Int. Cl.$^2$ .................. G01N 27/56; C07D 251/32
[52] U.S. Cl. .................. 204/1 T; 204/195 M; 544/223
[58] Field of Search .......... 544/223; 204/195 M, 204/1 N, 1 K

[56] References Cited

U.S. PATENT DOCUMENTS

| 3,539,455 | 11/1970 | Clark, Jr. | 204/1 T |
| 3,795,589 | 3/1974 | Dahms | 204/1 T |

OTHER PUBLICATIONS

Jiri Koryta, "Ion-Selective Electrodes", p. 57, (1975).

R. W. Cattrall et al., Anal. Chem., vol. 43, No. 13, pp. 1905–1906, (1971).

Helen James et al., Anal. Chem., vol. 44, No. 4, pp. 856–857, (1972).

Henry Freiser, Research/Development, pp. 28–33, Dec. 1976.

*Primary Examiner*—G. L. Kaplan
*Attorney, Agent, or Firm*—Robert W. Kell; Frank Ianno

[57] ABSTRACT

An electrode that is specific for the isocyanurate ion, and capable of rapid determination of the free isocyanurate ion activity directly in solution uses as its sensing element a platinum wire covered with a polyvinyl chloride membrane. The membrane is plasticized with a solution of a quaternary ammonium salt of isocyanuric acid. When this electrode and a commercial reference electrode are immersed in a solution containing the isocyanurate ion, a differential voltage proportional to the isocyanurate ion concentration is generated which is detected by a pH meter.

13 Claims, 7 Drawing Figures

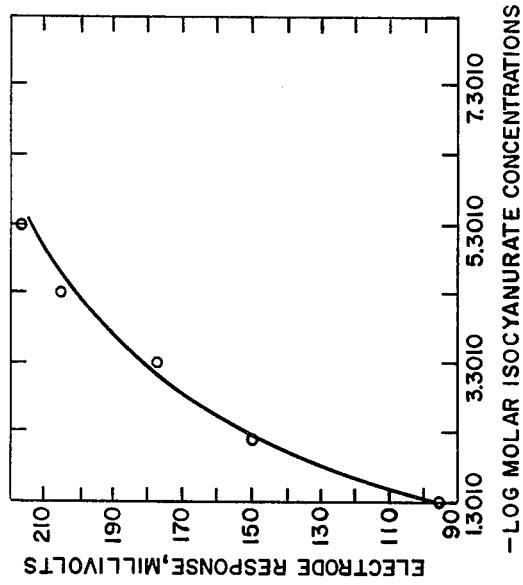
FIG. 5 CALIBRATION OF COATED WIRE ELECTRODE
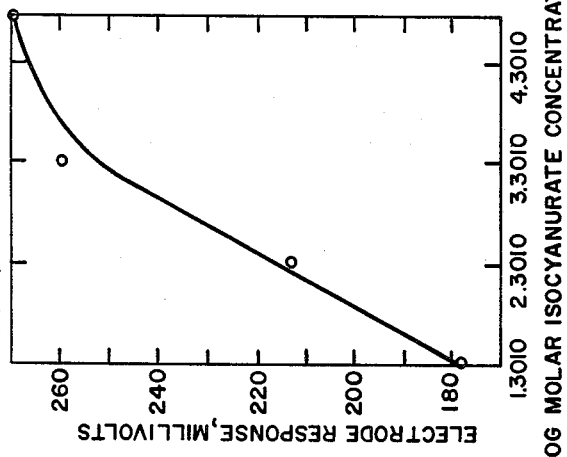
FIG. 4
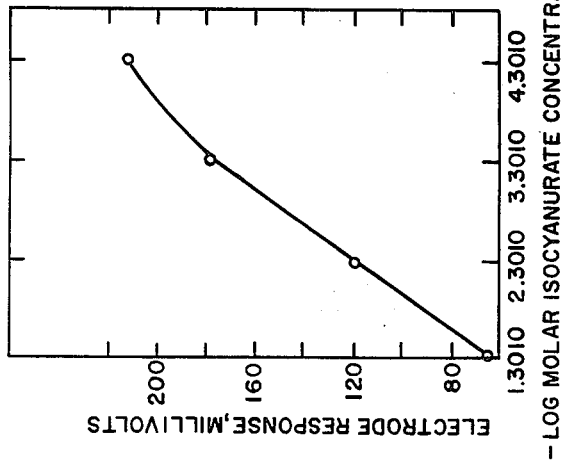
FIG. 3
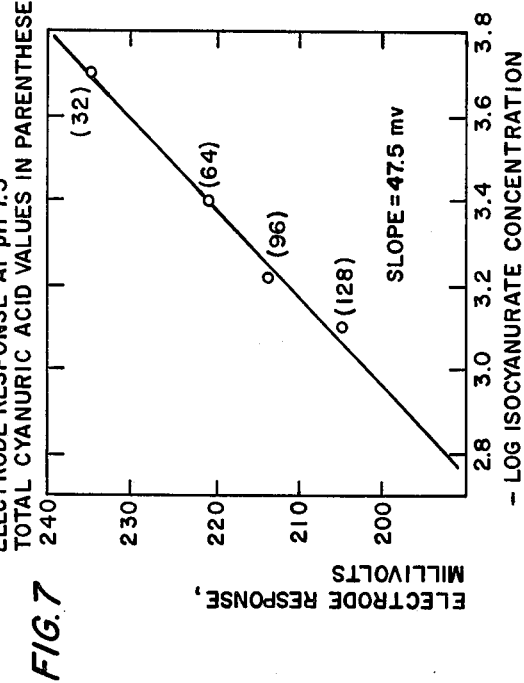
FIG. 7
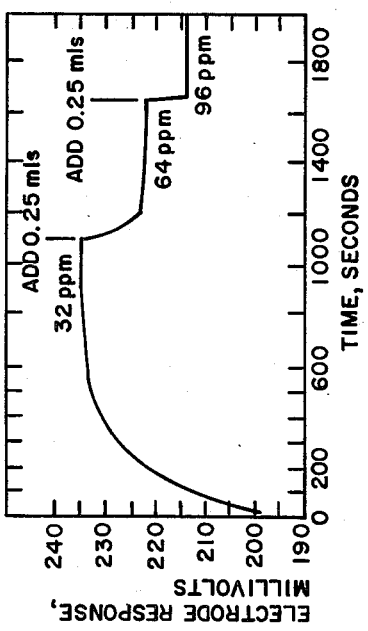
FIG. 6

ISOCYANURATE SPECIFIC ELECTRODE AND METHOD OF ANALYSIS AND QUATERNARY AMMONIUM ISOCYANURIC ACID SALTS THEREFORE

There has long been a need for a rapid, simple and effective method of determining the concentration of cyanurate compounds in solution. Such information is useful in the maintenance of swimming pools, the automation of cyanurate manufacturing operations and the monitoring of waste streams. Although electrochemical techniques such as chronopotentiometry have been used to analyze cyanuric acid, they all involve applying a voltage to the solution via an electrode and measuring the current that flows through the solution. The current is proportional to the ion concentration and there is nothing particular to the apparatus that makes the measurement specific for any one component in the solution.

The speed with which electrochemical determinations are made represents a unique advantage in qualitative and quantitative determination of various materials. As is well known, the accuracy of an electrochemical cell for analytical work depends upon the interrelation of the electrodes constituting the cell, the electrolyte, and to a great extent the substance being tested. As indicated above, however, the use of an electrochemical cell in chemical analysis is complicated by the fact that interfering substances may provide an erroneous electrical indication.

Numerous attempts have been made to avoid the adverse effect of materials which inherently interfere with the electrical measurement of a cell, i.e., provide a false current reading.

A compensated polarographic cell useful in the determination of an electrochemically inactive substance such as glucose in the presence of interfering ions is described by L. G. Clark, Jr., in British Pat. No. 1,167,317, and U.S. Pat. No. 3,539,455.

Electrochemical cells for the measurement of selected components such as sulfur dioxide are described by Harold Dahms in U.S. Pat. No. 3,795,589.

"Ion Selective Electrodes" by Jiri Koryta, Cambridge Monographs in Physical Chemistry 2. General Editors J. W. Linnett and J. H. Purnell, Cambridge University Press, Cambridge, 1975; provides a comprehensive treatment of the theory, properties, construcion and application of ion selective electrodes.

That a platinum wire coated with a polyvinyl chloride solution of calcium didodecylphosphate will function as a calcium ion selective electrode is described by Cattrall and Freiser, Analytical Chemistry 43, 1905 (1971). This approach was later extended to other anions of organic and biochemical interest, Analytical Chemistry 44, 856 (1972).

A platinum wire electrode coated with a solution of polyvinyl chloride and an ALIQUAT ® salt in decanol is described by Henry Freiser in Research and Development pages 28-33, December 1976. However, none of the electrodes described by earlier workers in this art have any utility in the determination of isocyanurate ions.

In accordance with the present invention, an electrode specific for the isocyanurate ion and capable of determining isocyanurate activity in solution is prepared by covering a platinum conductor with a plasticized polyvinyl chloride composition containing a quaternary ammonium isocyanurate salt. Suitable quaternary ammonium salts for use in the practice of this invention are those having the formula:

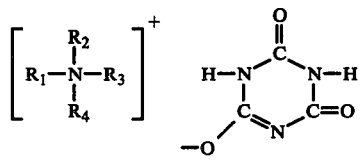

wherein $R_1$, $R_2$, $R_3$ and $R_4$ are alkyl radicals of 1 to 18 carbon atoms and the total number of carbon atoms in all of the alkyl radicals is such that the quaternary ammonium salt is soluble in decanol. Preferably, the total number of carbon atoms in all of the alkyl radicals is not less than eight.

The quaternary ammonium salt does not have to be isolated. It may be prepared by exchange between two immiscible phases and isolated in a plasticizer for polyvinyl chloride. Subsequent mixing of this plasticizer with a polyvinyl chloride solution will result in a coating composition suitable for preparation of a platinun electrode specific for the isocyanurate ion. Alternatively the quaternary ammonium salt may be milled with the polyvinyl chloride to disperse the salt uniformly throughout the polyvinyl chloride resin. The electrode of the present invention may be used in an electrochemical method of analyzing a solution for the isocyanurate ion.

The sensitivity of the new electrochemical method for isocyanurate analysis may be demonstrated by measuring the potential developed by the solution over four orders of magnitude is isocyanurate concentration. The electrode gives a linear response from the highest concentrations possible (a saturated solution) to as low as 10 parts per million, and even lower concentrations are within a useful working range. The response time is very short, from just a few seconds to minutes in some cases. Typical interfering ions such as chloride do not pose a problem and the effect of others can be easily determined as required. The analytical method to be described is capable of detecting cyanuric acid near neutral pH where the predominant form is its mono anion.

The actual measurement by the electrode is of the isocyanurate anion activity. This means that only free or uncombined isocyanurate ion is detectable. This differs from other existing measurements which interfere with solution equilibria and attempt to measure all the cyanuric acid, no matter which form it is in or how it is combined with other ions, metals, or organic compounds in solution. The non-destructive or passive measurement of the free ion activity opens up completely new possibilities for investigating chemical equilibria in real solutions and automating the long and tedious analytical methods presently used.

Accordingly, it is a primary object of the present invention to provide an improved electrode for the rapid and accurate quantitative determinations of the isocyanurate ion in solution.

Other objects and advantages of the present invention will be apparent from the following description, the accompanying drawings and the appended claims. In the drawings:

FIG. 3 is a calibration curve for the electrode illustrated in FIG. 1;

FIG. 4 is a calibration curve for the electrode illustrated in FIG. 2, wherein the membrane contains tetrabutyl ammonium iodide isocyanurate as described below in Example 2;

FIG. 5 is a calibration curve for the electrode illustrated in FIG. 2, wherein the membrane contains tricaprylylmethyl ammonium isocyanurate prepared as described below in Example 3;

FIG. 6 is a graph which shows the response time when immersed in a synthetic swimming pool water at pH 7.5 of the electrode described in Example 3; and FIG. 7 is a graph which shows the electrode response when immersed in a synthetic swimming pool water at pH 7.5 of the electrode described in Example 3.

Figure 1:
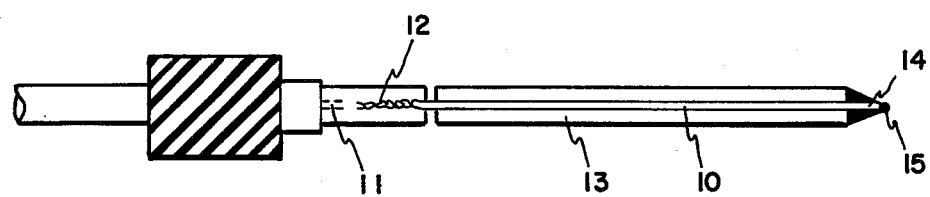
FIG. 1 is a schematic drawing of an isocyanurate specific electrode of the present invention.

The following Examples serve to further illustrate preparation of the electrodes of this invention.

EXAMPLE 1

A solution of a quaternary isocyanurate salt in decanol is prepared by dissolving 60 parts by weight of tricaprylylmethyl ammonium chloride (ALIQUAT 336S ®, manufactured by Pfaltz and Bauer, 375 Fairfield Avenue, Stamford, Connecticut 06902) in 40 by weight of decanol.

A saturated solution of sodium isocyanurate is prepared by stirring an excess of sodium isocyanurate with distilled water at room temperature while maintaining the pH at 9.0. The undissolved sodium isocyanurate is permitted to settle and the saturated solution is decanted from the residual solids. To 15 milliliters of this saturated sodium isocyanurate solution, in a separatory funnel, is added 5 grams of the decanol solution of tricaprylylmethyl ammonium chloride prepared as described in the preceding paragraph.

The separatory funnel is shaken by hand for 15 minutes and the aqueous solution is permitted to separated from the decanol solution. The aqueous phase is withdrawn from the separatory funnel and replaced by a fresh 15 milliliter portion of saturated sodium isocyanurate solution. Shaking is continued for another 15 minutes and the lower aqueous solution is again separated from the upper decanol layer containing the quaternary salt of the isocyanurate ion and discarded.

A solution of polyvinyl chloride in cyclohexanone is prepared by dissolving 8 grams of polyvinyl chloride characterized by a molecular weight of about 5,000 (GEON 121 ®, manufactured by B. F. Goodrich Company of Akron, Ohio) in 92 milliliters of cyclohexanone (J. T. Baker Analytical Grade). To 3 grams of this polyvinyl chloride solution is added with stirring 1 gram of the decanol solution of tricaprylylmethyl ammonium isocyanurate prepared as described above. The resulting viscous mixture is stirred well and used to coat the electrode illustrated in FIG. 1.

Referring now to FIG. 1, there is shown an isocyanurate specific electrode constructed by silver soldering a platinum wire 10 (0.010 inches in diameter) to a shielded coaxial cable 11 terminated at the other end with a typical pH plug-in connector. A soldered connection is shown at point 12. A section of TYGON ® tubing 13 having an internal diameter of 0.010 inches is placed over the platinum wire to insulate the wire from any solution in which the electrode might be placed. The length of the tubing 13 is such that the distal end 14 of the platinum wire projects beyond the end of the tubing a distance of about 0.20 inches.

The end of the platinum wire which extends beyond the TYGON ® tubing is dipped in the viscous mixture of polyvinyl chloride in cyclohexanone and tricaprylylmethyl ammonium chloride in decanol prepared as described above, to form a resin coating or membrane 15 about the end of the wire that extends beyond the TYGON ® tubing. After the membrane is dried, it may be stored in air indefinitely. Simple condition by immersion in the concentrated isocyanurate solution for about 15 minutes renders the electrode responsive to all of the test solutions. Daily calibration curves may be made to verify that the electrode is in acceptable condition.

A double junction reference electrode (ORION ® Model 90–02) the inner chamber of which is filled with a solution that matches the characteristics of a standard KCl calomel electrode (ORION ® solution 90-00-02) and the outer chamber of which contains a 10% solution of $KNO_3$ (ORION ® solution 90-00-03) is placed in a 100 milliliter beaker filled with a solution of sodium isocyanurate in distilled water (pH 9.0) containing $5 \times 10^{-2}$ moles of isocyanurate anion per liter. The electrode prepared as described above in this Example 1 is also immersed in the isocyanurate solution and the differential voltage measured with a digital pH meter (Model 701 manufactured by ORION Research, Inc., 380 Putnam Avenue, Cambridge, Massachusetts 02139). The differential voltage at equilibrium is 64 millivolts.

Successive dilutions of the sodium isocyanurate solution with distilled water gave the following voltage readings under equilibrium conditions.

TABLE I

| Isocyanurate Concentrations Moles of anion per liter | Millivolts |
| --- | --- |
| $5 \times 10^{-2}$ | 64 |
| $5 \times 10^{-3}$ | 120 |
| $5 \times 10^{-4}$ | 179 |
| $5 \times 10^{-5}$ | 213 |

The calibration curve for this electrode is shown in FIG. 3.

EXAMPLE 2

A saturated solution of a quaternary isocyanurate salt in decanol is prepared by mechanically stirring an excess of tetrabutyl ammonium iodide with 40 parts by weight of decanol at room temperature for 15 minutes and filtering to remove undissolved solids.

A saturated solution of sodium isocyanurate is prepared by stirring an excess of sodium isocyanurate with distilled water at room temperature while maintaining the pH at 9.0. The undissolved sodium isocyanurate is permitted to settle and the saturated solution is decanted from the residual solids. To 20 milliliters of this saturated sodium isocyanurate solution in a separatory funnel is added 3 grams of the decanol solution of tetrabutyl ammonium iodide prepared as described in the preceding paragraph.

The separatory funnel is shaken mechanically for 15 minutes and the aqueous solution is permitted to separate from the decanol solution. The aqueous phase is withdrawn from the separatory funnel and replaced by a fresh 20 milliliter portion of saturated sodium isocyanurate solution. Shaking is continued for another 15 minutes and the lower aqueous solution is again separated from the upper decanol layer containing the quaternary salt of the isocyanurate ion and discarded.

A solution of polyvinyl chloride in cyclohexanone is prepared by dissolving 8 grams of polyvinyl chloride characterized by a molecular weight of about 5,000 (GEON 121 ®, manufactured by B. F. Goodrich Company of Akron, Ohio) in 92 milliliters of cyclohexanone (J. T. Baker Analytical Grade). To 3 grams of this polyvinyl chloride solution is added with stirring 2 grams of the decanol solution of tetrabutyl ammonium isocyanurate prepared as described above. The resulting viscous mixture is stirred well, poured into an aluminum dish and dried to form a membrane. The membrane so obtained in used to modify a commercially available redox electrode of the type illustrated in FIG. 2.

Figure 2:
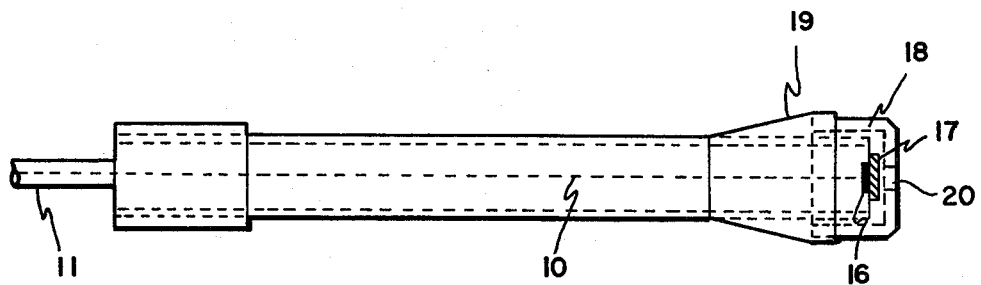
FIG. 2 is a schematic drawing of a commercially available redox platinum electrode modified in accordance with the present invention to respond specifically to the isocyanurate anion.

Referring now to FIG. 2, there is shown a platinum redox electrode having positioned at one end thereof a platinum disk 16 in electrical contact with a platinum wire 10. A shielded coaxial cable 11 is silver soldered to the other end of the platinum wire and fitted at its remote end with a typical pH plug-in connector. A small piece of the plasticized polyvinyl chloride membrane containing tetrabutyl ammonium isocyanurate 17, prepared as described above is cut to overlap the platinum disk 16 on the electrode body. The membrane 17 is pushed up tightly against the platinum and held in that position with a plastic cap 18 and electrical tape 19. A circular opening 20 in the end of cap 18 permits contact with the membrane of any solution into which the electrode is immersed. The type of electrode illustrated in FIG. 2 is more rugged than the electrode illustrated in FIG. 1 as the polyvinyl chloride membrane 17 is protected against mechanical abuse by the plastic cap.

The electrode prepared as described above in this Example is calibrated against a double junction electrode in a sodium isocyanurate solution (pH 9.0) in accordance with the procedure of Example 1 above. Successive dilutions of the sodium isocyanurate solutions with distilled water gave the following voltage readings under equilibrium conditions:

TABLE II

| Isocyanurate Concentrations Moles of Anion per liter | Millivolts |
| --- | --- |
| $5 \times 10^{-2}$ | 179 |
| $5 \times 10^{-3}$ | 214 |
| $5 \times 10^{-4}$ | 260 |
| $5 \times 10^{-5}$ | 270 |

The calibration curve for this electrode is shown in FIG. 4.

EXAMPLE 3

A solution of a quaternary isocyanurate salt in decanol is prepared by dissolving 60 parts by weight of tricaprylylmethyl ammonium chloride in 40 parts by weight of decanol.

A saturated solution of sodium isocyanurate is prepared by stirring an excess of sodium isocyanurate with distilled water at room temperature while maintaining the pH at 9.0. The undissolved sodium isocyanurate is permitted to settle and the saturated solution is decanted from the residual solids. To 15 milliliters of this saturated sodium isocyanurate solution in a separatory funnel is added 5 grams of the decanol solution of tricaprylylmethyl ammonium chloride prepared as described in the preceding paragraph.

The separatory funnel is shaken by hand for 15 minutes and the aqueous solution is permitted to separated from the decanol solution. The aqueous phase is withdrawn from the separatory funnel and replaced by a fresh 15 milliliter portion of saturated sodium isocyanurate solution. Shaking is continued for another 15 minutes and the lower aqueous solution is again separated from the upper decanol layer containing the quaternary salt of the isocyanurate ion.

A solution of polyvinyl chloride is cyclohexanone is prepared by dissolving 8 grams of polyvinyl chloride characterized by a molecular weight of about 5,000 (GEON 121 ®, manufactured by B. F. Goodrich Company of Akron, Ohio) in 92 milliliters of cyclohexanone (J. T. Baker Analytical Grade). To 5 grams of this polyvinyl chloride solution is added with stirring 1 gram of the decanol solution of tricaprylylmethyl ammonium isocyanurate prepared as described above in this Example. The resulting viscous mixture is stirred well, poured into an aluminum dish and dried to form a membrane. The membrane so obtained is used to modify a commercially available redox electrode of the type illustrated in FIG. 2 as described in the preceding Example 2.

The electrode prepared as described above in this Example is calibrated against a double junction electrode in a sodium isocyanurate solution (pH 9.0) in accordance with the procedure outlined in Example 1 above. Successive dilutions of the sodium isocyanurate solutions with distilled water gave the following voltage readings under equilibrium conditions:

TABLE III

| Isocyanurate Concentrations Moles of Anion per liter | Millivolts |
| --- | --- |
| $5 \times 10^{-2}$ | 96 |
| $5 \times 10^{-3}$ | 150 |
| $5 \times 10^{-4}$ | 178 |
| $5 \times 10^{-5}$ | 206 |
| $5 \times 10^{-6}$ | 218 |

The calibration curve for this electrode is shown in FIG. 5.

EXAMPLE 4

A synthetic swimming pool water stock solution is prepared by dissolving 0.05 moles of sodium cyanurate in a liter of distilled water containing 80 ppm of sodium carbonate and 80 ppm calcium chloride. The pH is adjusted to 7.5 with 0.1 normal sodium hydroxide. One milliliter of this stock solution is diluted with distilled water to 200 milliliters (32 ppm cyanurate ion) and the differential voltage determined as described above in Example 1 on a 50 milliliter sample of the diluted stock solution. The response time (elapsed time required after immersion to obtain 95% of the final constant voltage reading) is approximately 200 seconds.

As best shown in FIGS. 6 and 7, the addition of 0.25 milliliters of the undiluted stock solution to the 50 milliliter sample increases the cyanurate ion concentration to 64 ppm and reduces the differential voltage from 235 millivolts to 222 millivolts. The response time is less than 70 seconds. A second addition of 0.25 milliters of the undiluted stock solution to the 50 milliliter sample increases the cyanurate ion concentration to 96 ppm and reduces the differential voltage to 213 millivolts. The response time is less than 10 seconds.

The response time (in seconds) of the electrode described in Examples 1—3 has been found to vary with the concentration of isocyanurate ions as summarized in Table IV.

TABLE IV

| | Response Time in Seconds at pH 9.0 | | | | |
|---|---|---|---|---|---|
| | Concentration of Isocyanurate Ion moles per liter | | | | |
| Electrode | $5 \times 10^{-2}$ | $5 \times 10^{-3}$ | $5 \times 10^{-4}$ | $5 \times 10^{-5}$ | $5 \times 10^{-6}$ |
| Example 1 | 300 | 1000 | 200 | 700 | 700 |
| Example 2 | 30 | 30 | 30 | 30 | — |
| Example 3 | 50 | 50 | 30 | 30 | 20 |

The response time increases considerably when sodium chloride is present at 0.05 molar concentration.

EXAMPLE 5

The selectivity coefficient $K_{CA,I}$ is a measure of the ability of an electrode to respond accurately to a specific ion in the presence of another potentially interfering ion, and is defined by the equation:

$$E = \text{constant} + \text{SLOPE} \log [A_{CA} + K_{CA,I}(A_I)^{1/Z}]$$

wherein $A_{CA}$ is the isocyanurate ion molar activity, $A_I$ is the interfering ion molar activity, and Z is the valence of the interfering ion. Values of $K_{CA,I}$ are determined for sodium chloride and sodium bicarbonate/carbonate which are typical electrolytes and potential interferents in swimming pool water that uses cyanuric acid as a chlorine stabilizer. Solutions of varying isocyanuric acid molar activity are prepared containing a constant interfering ion concentration (0.050 molar sodium chloride).

A second series of solutions of varying isocyanuric acid molar activity is prepared containing a constant interfering ion concentration (0.0050 molar sodium bicarbonate/carbonate).

The observed differential voltages determined as described in Example 1 above by immersing the electrode of that Example in the solutions described in the two preceding paragraphs are summarized in Table V.

$$E = \text{Constant} + \text{SLOPE} \log [A_{CA} + K_{(A,I)}^{1/Z}]$$

and solving for K gives the selectivity coefficients summarized in Table VI.

TABLE V

| Isocyanurate Concentration | 0.050 Moles Sodium Chloride-Millivolts | 0.0050 Moles Bicarbonate/ Carbonate-Millivolts |
|---|---|---|
| $5 \times 10^{-2}$ | 162 | 125 |
| $5 \times 10^{-3}$ | 225 | 177 |
| $5 \times 10^{-4}$ | 277 | 202 |
| $5 \times 10^{-5}$ | 285 | 201 |

TABLE VI

| | Selectivity Coefficients, K | | |
|---|---|---|---|
| Interfering | Isocyanurate Concentration, moles per liter | | |
| Ion | $5 \times 10^{-2}$ | $5 \times 10^{-3}$ | $5 \times 10^{-4}$ |
| Chloride (0.0500 molar) | 0.325 | 0.0031 | 0.0027 |
| Bicarbonate (0.0050 molar) | 1.9 | 0.022 | 0.23 |

EXAMPLE 6

The concentration of cyanuric acid in swimming pool water is determined as described above in Example 1 by placing the electrode and reference electrode of that Example in a 500 milliliter beaker containing a 250 milliliter sample of the water to be tested adjusted to pH 7.5. The differential voltage between electrodes is constant after 4 minutes at 220 millivolts.

The electrode and reference electrode are then calibrated against a synthetic swimming pool water prepared as described above in Example 4 at 32 ppm, 64 ppm, and 96 ppm cyanurate ion concentration and a calibration curve prepared as illustrated in FIG. 6. The negative log of the concentration of cyanuric acid in the swimming pool water is read from the intersection of the observed voltage with the calibration curve and the cyanurate ion concentration is calculated from the negative log to be 67 ppm.

While the electrodes and the methods herein described constitute preferred embodiments of the invention, it is to be understood that the invention is not limited to those precise forms of electrodes and the methods may be modified without departing from the scope of the invention.

What is claimed is:

1. An electrode specific for the isocyanurate ion and capable of determining isocyanurate ion activity in solutions comprising:
   (a) a platinum conductor covered with a plasticized polyvinyl chloride composition containing a quaternary ammonium isocyanurate salt;
   (b) means for electrically connecting the platinum conductor to a pH meter, and
   (c) means for insulating said platinum conductor from said solution.

2. An electrode specific for the isocyanurate ion and capable of determining isocyanurate ion activity in solutions comprising a platinum surface, portion of which is covered with a plasticized polyvinyl chloride composition containing a quaternary ammonium isocyanurate salt, said surface which is not covered with said composition being covered by a substance that is impermeable to water and electrical conducting means attached to said electrode.

3. The electrode of claim 2 wherein said platinum is electrically connected to a shielded coaxial cable.

4. An electrode specific for the isocyanurate ion and capable of determining isocyanurate ion activity in solutions comprising a centrally located platinum wire one end of which is coated with a plasticized polyvinyl chloride composition containing a quaternary ammonium isocyanurate salt, said wire being surrounded from the coated end for a distance along the length of the wire by a substance that is impermeable to water.

5. The electrode of claim 4 wherein the other end of said platinum wire is electrically connected to a shielded coaxial cable.

6. A platinum redox electrode that has been modified by covering that part of the platinum that is exposed with a plasticized polyvinyl chloride composition containing a quaternary ammonium isocyanurate salt.

7. An electrochemical method of analyzing an aqueous solution for isocyanurate ion which comprises:
   (a) immersing a reference electrode and a platinum electrode covered with a plasticized polyvinyl chloride resin containing a quaternary ammonium isocyanurate salt in a series of aqueous solutions containing known molar concentrations of isocyanurate ions;
   (b) measuring the difference in potential between the reference electrode and covered platinum electrode when immersed in each of said solutions;

(c) preparing a calibration curve by plotting a function of the molar isocyanurate concentration of each solution against the differential potential developed in that solution;

(d) immersing said reference electrode and said platinum electrode in an unknown aqueous solution to be analyzed for isocyanurate activity and measuring the differential voltage developed; and (e) determining from the measured differential voltage and the calibration curve the concentration of isocyanurate ion in said unknown aqueous solution.

8. The method of claim 7 wherein the quaternary ammonium salt is tricaprylylmethyl ammonium isocyanurate.

9. The method of claim 7 wherein the quaternary ammonium salt is tetrabutyl ammonium isocyanurate.

10. The method of claim 7 wherein the plasticizer is decanol.

11. A quaternary isocyanuric acid salt having the formula:

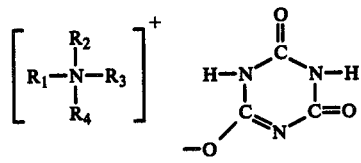

wherein $R_1$, $R_2$, $R_3$, and $R_4$ are alkyl radicals of 1 to 18 carbon atoms and the total number of carbon atoms in all of the alkyl radicals is such that the quaternary ammonium salt is soluble in decanol.

12. The quaternary isocyanuric acid salt of claim 11 wherein $R_1$, $R_2$, $R_3$ and $R_4$ are butyl radicals.

13. The quaternary isocyanuric acid salt of claim 11 wherein $R_1$, $R_2$ and $R_3$ are caprylyl radicals and $R_4$ is a methyl radical.

UNITED STATES PATENT AND TRADEMARK OFFICE
CERTIFICATE OF CORRECTION

PATENT NO. : 4,134,798
DATED : January 16, 1979
INVENTOR(S) : Michael L. Pinsky

It is certified that error appears in the above-identified patent and that said Letters Patent are hereby corrected as shown below:

Column 2, line 35, "is" should read --in--. Column 3, lines 29-30, "40 by weight" should read --40 parts by weight--; line 42, "separated" should read --separate--. Column 6, line 2, "separated" should read --separate--; line 10, "is" should read --in--. Column 7, between lines 41-42, the following was omitted --Substituting these values in the equation:--.

Signed and Sealed this

Nineteenth Day of June 1979

[SEAL]

Attest:

RUTH C. MASON
Attesting Officer

DONALD W. BANNER
Commissioner of Patents and Trademarks